United States Patent
Tang (10) Patent No.: US 10,034,784 B2
(45) Date of Patent: Jul. 31, 2018

(54) HEART VALVE AND ENDOVASCULAR GRAFT COMPONENTS AND METHOD FOR DELIVERY

(71) Applicant: Gilbert H. L. Tang, New York, NY (US)

(72) Inventor: Gilbert H. L. Tang, New York, NY (US)

(*) Notice: Subject to any disclaimer, the term of this patent is extended or adjusted under 35 U.S.C. 154(b) by 127 days.

(21) Appl. No.: 14/255,853

(22) Filed: Apr. 17, 2014

(65) Prior Publication Data

US 2014/0316513 A1  Oct. 23, 2014

Related U.S. Application Data

(60) Provisional application No. 61/854,035, filed on Apr. 17, 2013, provisional application No. 61/854,036, filed on Apr. 17, 2013.

(51) Int. Cl.
| | | |
|---|---|---|
| A61F 2/852 | (2013.01) | |
| A61F 2/07 | (2013.01) | |
| A61F 2/24 | (2006.01) | |
| A61F 2/89 | (2013.01) | |
| A61F 2/06 | (2013.01) | |

(52) U.S. Cl.
CPC .......... *A61F 2/852* (2013.01); *A61F 2/07* (2013.01); *A61F 2/2412* (2013.01); *A61F 2/2418* (2013.01); *A61F 2/89* (2013.01); *A61F 2002/061* (2013.01); *A61F 2220/0025* (2013.01); *A61F 2230/0043* (2013.01); *A61F 2250/0063* (2013.01)

(58) Field of Classification Search
CPC .... A61F 2/07; A61F 2/89; A61F 2/852; A61F 2/2412; A61F 2/2418; A61F 2002/061; A61F 2002/0025; A61F 2002/0063; A61F 2002/0043; A61F 2/04; A61F 2/82; A61F 2002/823; A61F 2002/072; A61F 2002/075; A61F 2002/077; A61F 2002/065; A61F 2/856; A61F 2220/0025; A61F 2230/0043; A61F 2250/0063
See application file for complete search history.

(56) References Cited

U.S. PATENT DOCUMENTS

| | | | |
|---|---|---|---|
| 5,824,064 A | 10/1998 | Taheri | |
| 5,906,640 A * | 5/1999 | Penn | ......... A61F 2/91 623/1.15 |
| 6,099,548 A | 8/2000 | Taheri | |
| 6,723,116 B2 | 4/2004 | Taheri | |
| 6,918,925 B2 | 7/2005 | Tehrani | |
| 6,949,121 B1 * | 9/2005 | Laguna | ......... A61F 2/07 623/1.35 |
| 7,261,732 B2 | 8/2007 | Justino | |
| 7,854,758 B2 | 12/2010 | Taheri | |

(Continued)

*Primary Examiner* — Christopher D Prone
*Assistant Examiner* — Rokhaya Diop
(74) *Attorney, Agent, or Firm* — Stephen Kenny; Foley Hoag LLP (57) ABSTRACT

A medical device including a valve member with an elongate tubular portion with at least one aperture disposed in a sidewall at a location between the proximal and distal ends, and a plurality of leaflets; a first endovascular graft coupled to the valve member; and a second endovascular graft coupled to the first endovascular graft; and an expandable anchor member coupled to the second endovascular graft.

16 Claims, 9 Drawing Sheets

(56) References Cited

U.S. PATENT DOCUMENTS

| | | |
|---|---|---|
| 7,918,885 B2 | 4/2011 | Sievers et al. |
| 8,092,511 B2 | 1/2012 | Chuter |
| 8,167,930 B2 | 5/2012 | Allen et al. |
| 2005/0222674 A1 | 10/2005 | Paine |
| 2006/0195177 A1 | 8/2006 | Kaufmann et al. |
| 2006/0247757 A1 | 11/2006 | Kaufmann et al. |
| 2009/0125098 A1 | 5/2009 | Chuter |
| 2009/0264993 A1 | 10/2009 | Greenan |
| 2009/0270965 A1 | 10/2009 | Sinha et al. |
| 2010/0087907 A1 | 4/2010 | Lattouf |
| 2011/0224780 A1* | 9/2011 | Tabor ............... A61F 2/013 623/1.24 |
| 2012/0046726 A1 | 2/2012 | Chuter |
| 2012/0130472 A1 | 5/2012 | Shaw |
| 2012/0158121 A1 | 6/2012 | Greenberg et al. |
| 2012/0197382 A1* | 8/2012 | Roeder ............... A61F 2/07 623/1.13 |
| 2012/0221094 A1 | 8/2012 | Cunningham et al. |
| 2013/0018449 A1 | 1/2013 | Bailey et al. |
| 2013/0144373 A1* | 6/2013 | Shahriari ............ A61F 2/07 623/1.12 |

* cited by examiner

HEART VALVE AND ENDOVASCULAR GRAFT COMPONENTS AND METHOD FOR DELIVERY

CROSS REFERENCE TO RELATED APPLICATIONS

This application claims the benefit of the priority of U.S. Provisional Patent Application Nos. 61/854,035 and 61/854,036 filed Apr. 17, 2013, each of which is incorporated herein by reference in its entirety.

BACKGROUND OF THE DISCLOSED SUBJECT MATTER

Field of the Disclosed Subject Matter

The disclosed subject matter relates to a system for treating endovascular irregularities and repair. Particularly, the present disclosed subject matter is directed to a medical device for use within the aorta.

Description of Related Art

Aortic aneurysms are a common deteriorating disease typically manifested by a weakening and expansion of the aorta vessel wall. Aneurysms affect the ability of the vessel lumen to conduct fluids, and may at times be life threatening when, for example, rupture of the vessel wall occurs. A standard treatment for repairing an aneurysm is to surgically remove part or all of the aneurysm and implant a replacement prosthetic section into the vessel.

Figure 1:
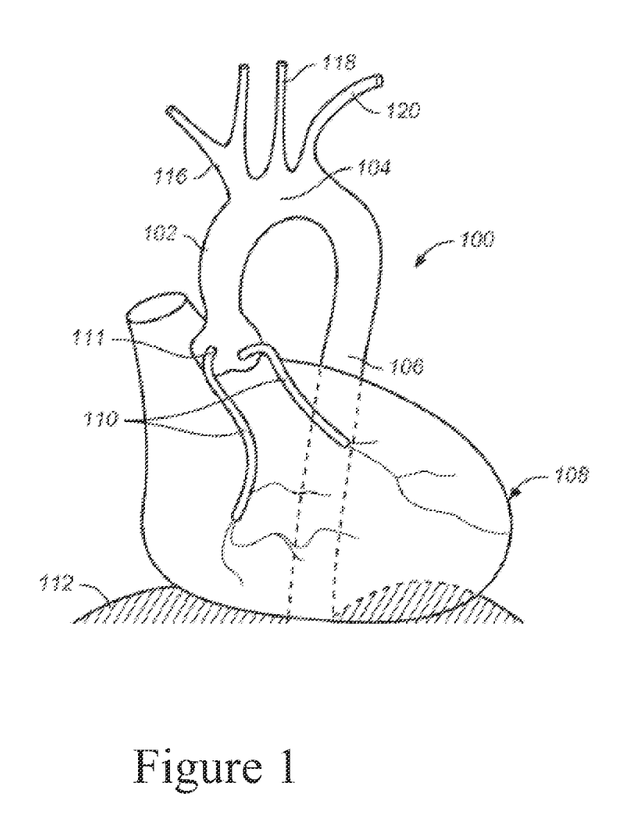
FIGS. 1-2 are schematic representations of the anatomy of the heart and aorta.

The aorta is the major artery that carries blood from the heart to the rest of the body. FIG. 1 is a schematic illustration of the aorta 100 and the heart 108. The aorta 100 includes an ascending aorta 102, an aortic arch 104, and a descending aorta 106. The ascending aorta 102 is the first segment of the aorta 100 where the aorta 100 originates from the heart's left ventricle. Coronary arteries 110 originate at the aortic root 111. The brachiocephalic artery 116, the left common carotid artery 118, and the left subclavian artery 120 branch from the aortic arch 104. The descending artery 106 extends past the diaphragm 112, leading to the abdominal aorta 114.

Figure 2:
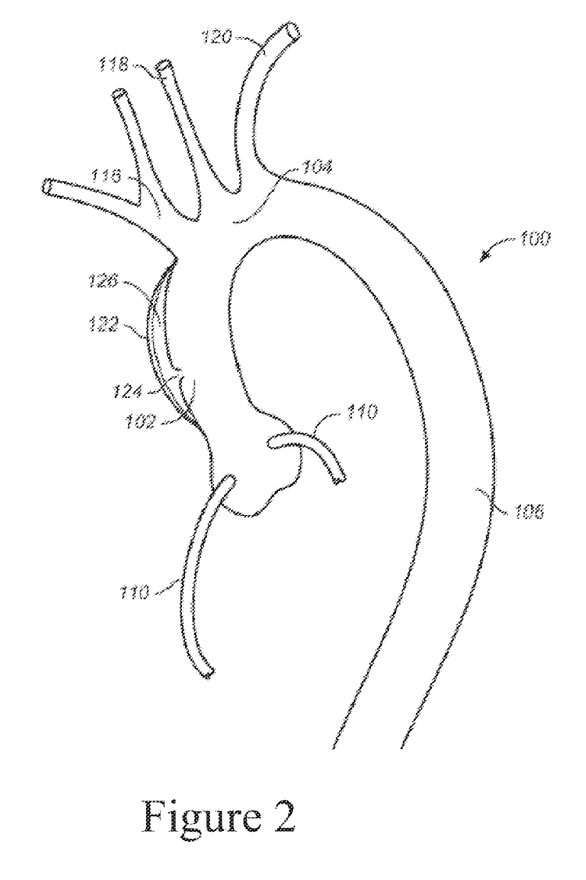

Aortic dissection occurs when the inner layer of the aorta's artery wall splits open (dissects). This is more likely to occur where pressure on the arterial wall from blood flow is high, such as in the ascending aorta 102. FIG. 2 shows a dissection 122 in the ascending aorta 102. The dissection may be caused by a tear 124 in the aortic wall. When the layers of the aortic wall split open (separate from one another), it creates a false lumen 126 through which pulsatile blood flow can access the inner layers that compose the arterial wall.

The flow of blood through this false lumen, and the resulting increase in pressure, can exacerbate the dissection and cause further tearing. The standard surgical approach in patients with ascending aortic aneurysm or dissection involving the aortic root and associated with aortic valve disease is open heart surgery including the replacement of the aortic valve and ascending aorta. Acute type A dissection is categorized as a surgical emergency with a 1% mortality per hour, and an average operative mortality of 30%. In patients who have multiple comorbidities, hemodynamic instability or malperfusion and end-organ dysfunction, aortic root replacement for the above indications carry significant operative mortalities and morbidities.

Numerous endovascular devices are known to treat varying aspects of heart valves and aortic root repair, including U.S. Patent Publication Nos. 2009/0270965, 2009/0264993, 2012/0130472, 2006/0195177 and U.S. Pat. No. 6,723,116, each of which is hereby incorporated by reference in its entirety.

There thus remains a need for a safe and effective method and system for an endovascular bioprosthetic valve-conduit as aortic root replacement in this acutely ill and high risk patient population. The device and methods disclosed herein can be implanted expediently via a catheter-based approach on a beating heart, avoiding potential morbidities associated with an open heart procedure.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a medical device comprising a valve member, the valve member including: an elongate tubular portion having a proximal end and a distal end defining a length therebetween, the elongate tubular portion having at least one aperture disposed in a sidewall at a location between the proximal and distal ends, and a plurality of leaflets. The device also includes a first endovascular graft having a proximal end and a distal end defining a length therebetween and an opening at the proximal and distal ends, the first endovascular graft configured for coupling to the valve member; and a second endovascular graft having a proximal end and a distal end defining a length therebetween and an opening at the proximal and distal ends, the second endovascular graft configured for coupling to the first endovascular graft; and an expandable anchor member, the expandable anchor member configured for coupling to the second endovascular graft.

In some embodiments, the elongate tubular portion of the valve member has a non-uniform geometry. Additionally, the proximal end and distal end of the elongate tubular portion of the valve member can be configured with a first diameter, and a midpoint of the elongate tubular portion of the valve member having a second diameter (e.g. such that the elongate tubular portion of the valve member has tapered contour). Also, the at least one aperture in the elongate tubular portion of the valve member is disposed proximate a midpoint between the proximal and distal ends of the elongate tubular portion.

The valve member and first endovascular graft can be formed as an integral unit, additionally or alternatively, the valve member, first endovascular graft, second endovascular graft, and expandable anchor member can be formed as separate components.

In some instances the valve member is self-expanding and the expandable anchor member is a self-expanding stent. Also, the second endovascular graft includes a sidewall aperture at a location disposed between the proximal and distal ends thereof, such that the expandable anchor member is in fluid communication with the sidewall aperture of the second endovascular graft. Further, a seal member can be disposed at a proximal end of the valve member.

In accordance with another aspect of the present disclosure, a medical device is provided comprising a valve member, the valve member including: a plurality of leaflets, adjacent leaflets joined at valve commissures, and an elongate tubular portion having a proximal end and a distal end defining a length therebetween and a graft material extending over at least a portion of the tubular portion, the elongate tubular portion having at least one aperture disposed in a sidewall at a location proximate the valve commissures. The device also includes a first endovascular graft having a proximal end and a distal end defining a length therebetween and an opening at the proximal and distal ends, the proximal end of the first endovascular graft configured for coupling to the valve member; wherein the proximal end and distal end of the elongate tubular portion of the valve member have a first diameter, and a midpoint of the elongate tubular portion of the valve member has a second diameter.

In some embodiments, the valve member and first endovascular graft are formed as an integral unit. Additionally, the device can include at least one coronary stent configured for coupling to the elongate tubular portion of the valve member, wherein the at least one coronary stent includes a flared end, the flared end coupled to the elongate tubular portion of the valve member.

In accordance with another aspect of the present disclosure, a medical device is provided comprising an aortic arch graft comprising a first generally cylindrical member having a proximal end and a distal end and a longitudinally extending lumen, the proximal end configured for deployment within the ascending aorta, the distal end configured for deployment in the descending thoracic aorta; and a graft material extending over a portion of the generally cylindrical member, the graft material having an opening disposed between the proximal end and distal end with a plurality of radiopaque markers disposed around a periphery of the opening; wherein the opening within the graft material allows blood flow transverse to the longitudinal lumen of the generally cylindrical member.

In some embodiments, the opening within the graft material is elliptical. Further, the device can include a first expandable anchor member partially extending into the proximal end of the generally cylindrical member, and a second expandable anchor member partially extending into the distal end of the generally cylindrical member. For example, the first and second expandable anchor members can be self-expanding stents.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

DETAILED DESCRIPTION OF AN
EXEMPLARY EMBODIMENT

Reference will now be made in detail to exemplary embodiments of the disclosed subject matter, an example of which is illustrated in the accompanying drawings. The method and corresponding steps of the disclosed subject matter will be described in conjunction with the detailed description of the system.

The methods and systems presented herein may be used to perform an aortic root replacement. The disclosed subject matter is particularly directed towards an endovascular bioprosthetic valve-conduit device that can be used in aortic root replacement, performed via a catheter-based approach on a beating heart, avoiding open heart surgery. Implanting such a device on a beating heart not only shortens procedural time, reducing morbidities associated with open heart surgery, and can be a life-saver in patients with multiple co-morbidities or who are critically ill where an open surgical procedure would carry significant or even prohibitive risks.

For purpose of explanation and illustration, and not limitation, an exemplary embodiment of the system, also registered as EndoRoot® with the U.S. Patent & Trademark Office, is shown in FIGS. 3-11. Similar reference numerals (differentiated by the leading numeral) may be provided among the various views and Figures presented herein to denote functionally corresponding, but not necessarily identical structures.

Figure 3:
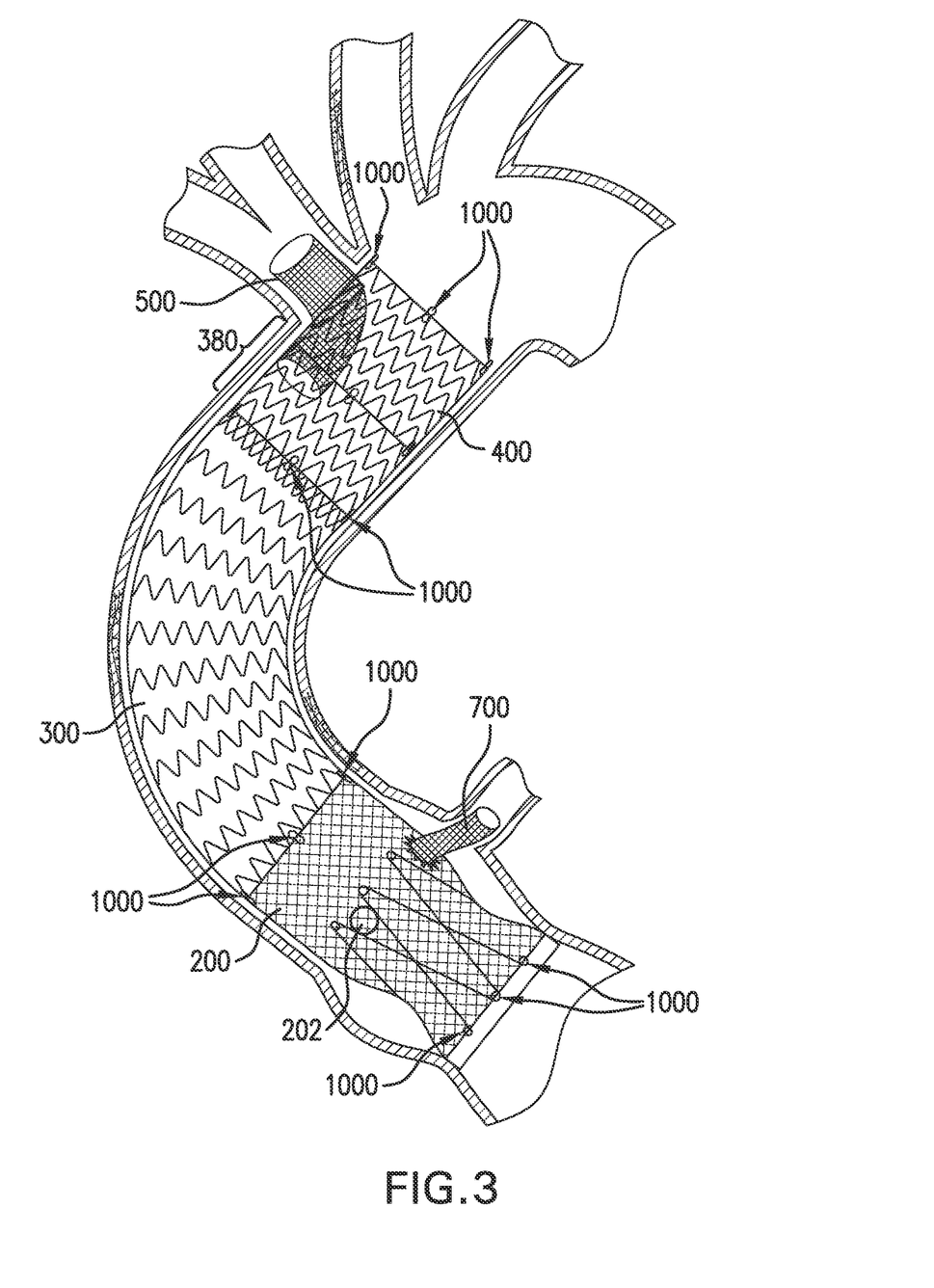
FIGS. 3-4 are schematic representations of the medical device disclosed herein, as deployed within a patient.

As shown in FIG. 3, the system generally includes a combination of at least one endovascular (e.g. stent) graft 300 and valve member (e.g. transcatheter heart valve) 200 with side coronary orifices 202 on the valve member to allow perfusion the coronary arteries during and after deployment. In some embodiments, additional endovascular (e.g. stent) grafts 700 are deployed to bridge the coronary ostia with the side orifices 202 of the valve member 200 to seal the blood from extravasating outside the implanted device(s) into the native aortic root. Additionally, in some embodiments an additional endovascular (e.g. brachiocephalic stent) graft 400 is configured with a side opening for receiving anchoring stent 500 which serves to anchor the entire device from the aortic root to the hemiarch.

The individual components disclosed herein can be formed as either as an integral unitary (composite) device, or as discrete members that are formed separately and assembled (either prior to deployment or after deployment within a patient). Additionally or alternatively, certain combinations of components can be formed as an integral unit while other components are discrete members configured to be assembled to the integral unit either prior to deployment or after deployment within a patient.

Endovascular Graft

Referring to the exemplary embodiment shown in FIGS. 3-7 and 10, the endovascular (e.g. stent) graft 300 is sized and shaped for insertion proximate the aortic root 111. The stent-graft 300 includes a distal end 322, a proximal end 324, and a main body 326 extending between the distal end 322 and the proximal end 324. It will be appreciated that the main body 326 is generally circular in cross-section so as to define a central lumen which provides a flow path for blood flowing through the aorta. The main body 326 of the stent-graft 300 includes a vascular graft and an underlying or interwoven expandable stent.

For purpose of illustration and not limitation examples of the graft material which can be employed on the various graft components disclosed herein can include synthetic, biodegradable or biological material such as Dacron®, Gore-Tex®, or any other suitable vascular graft material as would be known to those of skill in the art. The underlying, or interwoven, expandable members disclosed herein (e.g. stents) can be constructed of a wire mesh material, such as of stainless steel or Nitinol®. Additionally, the expandable member can be formed of a shape memory material.

In some embodiments, each of the distal end and the proximal ends of the various components can incorporate radio-opaque markers, thus enabling the location of the particular component (e.g. stent-graft) within the aorta to be determined using conventional diagnostic techniques such as, for example, X-rays, MRI, or CAT scan. Additionally or alternatively, a longitudinal bar with radio-opaque markers, to be deployed along the greater curvature of the ascending aorta, can be incorporated into the endovascular graft(s) to better approximate the native aortic anatomy and orientation. In the exemplary embodiments disclosed herein, the stent graft portion has four radio-opaque markers 1000 positioned 90 degrees apart at the proximal and distal ends. This allows for accurate placement with respect to the distal or proximal positioning of the stent graft, as well as for accurate circumferential positioning of the stent graft ends in the event the physician needs to rotate the stent graft with respect to one of the other components (e.g. valve member 200, brachiocephalic stent graft 400).

In the disclosed example, the stent is shown in a Z-shaped configuration, although other configurations (e.g. a series of annular rings with longitudinally extending connectors, or a criss-crossing configuration) may also be employed. The particular embodiments disclosed are for exemplary purposes, thus it is to be understood that other materials and structures for the stent may be used. Also, the stent graft portion(s) of the device, whether in an integral construction or multi-part configuration, can be formed within a range of lengths and diameters to be deployed and accommodate to the widest range of human anatomy. Additionally, each endovascular graft can be fully adjustable, fully repositionable, and fully retrievable during the delivery and deployment procedure (described in further detail below) such that it can return to its original fully expanded form after external compression without impact on structural integrity, radial and longitudinal strength and flow characteristics.

In some embodiments the endovascular graft 300 can include retention features (e.g. outwardly extending barbs) pointing in the distal direction to improve anchorage of the stent graft component 300 to the valve member 200. In some embodiments, as shown in FIG. 3, the adjacent ends of the endovascular graft 300 and valve member 200 are joined in an abutting relationship. In other embodiments, as described in further detail below and shown in FIG. 4, the endovascular graft 300 and valve member 200 are arranged in a partially overlapping region 280. In some embodiments, the overlapping region between the adjacent components is a distance of about 5 mm or greater. The amount of overlap can vary depending on the amount of coupling desired, provided the proximal end of the endovascular graft 300 does not extend to interfere with the flow of blood through valve apertures 202 or leaflets 252. In some instances, the amount of overlap can be greater than 5 mm if the adjacent (proximal) end of the endovascular graft 300 is a bare metal stent free of any graft material, thus reducing or eliminating the risk of occluding the valve apertures 202 and/or leaflets 252. The larger the amount of overlap, the stronger the coupling between the two components. In this regard, the endovascular graft 300 can have a larger (expanded) diameter than the valve member 200 to ensure an adequate (e.g. interference fit) seal.

Brachiocephalic Endovascular Graft

Figure 6:
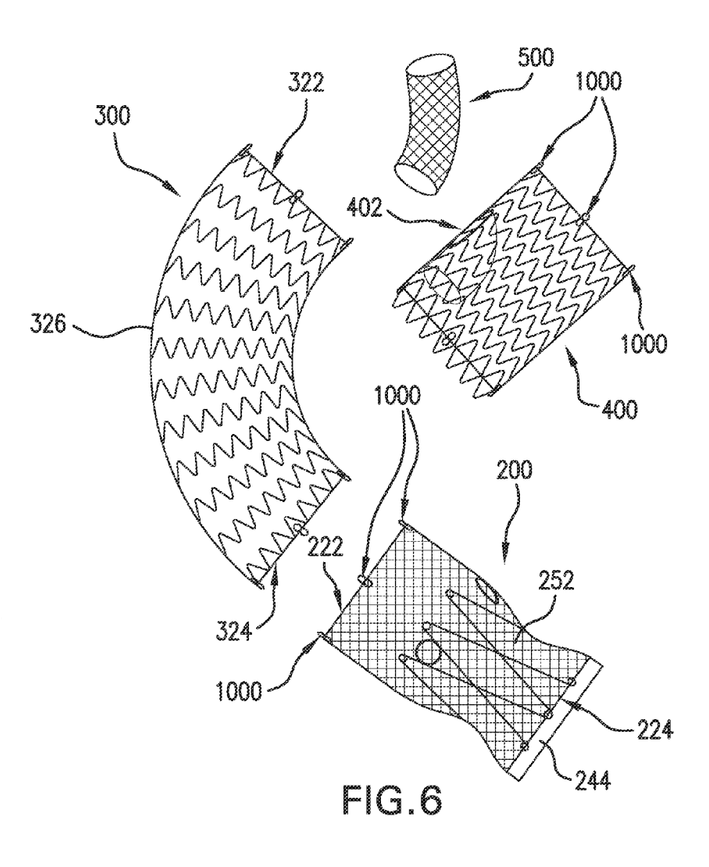

In accordance with another aspect of the disclosure, an optional additional endovascular graft can be employed and positioned distal to the endovascular graft 300. An exemplary embodiment of such an optional endovascular graft is shown in FIGS. 3-4 and 6 which depicts a brachiocephalic graft 400 with an aperture 402 configured to receive a brachiocephalic artery stent 500.

The brachiocephalic graft 400 can be constructed in a similar manner as the endovascular graft 300, as discussed above. The proximal end of the brachiocephalic graft 400 can be configured with structural retention features for coupling to the distal portion of the endovascular graft 300. In some embodiments these structural retention features include open flares for matingly engaging the frame (e.g. annular ring) of the expandable stent of the endovascular graft 300. Additionally or alternatively, the structural retention features can include magnetic couplers (one on each component to be joined) which connect the adjacent components together. For some applications the magnetic couplers can be advantageous as they can be formed coplanar (or "flush") with the component (e.g. within the struts comprising the brachiocephalic graft 400) and do not protrude radially outward which may cause tissue damage, or radially inward which can obstruct blood flow through the lumen of the graft.

Figure 4:
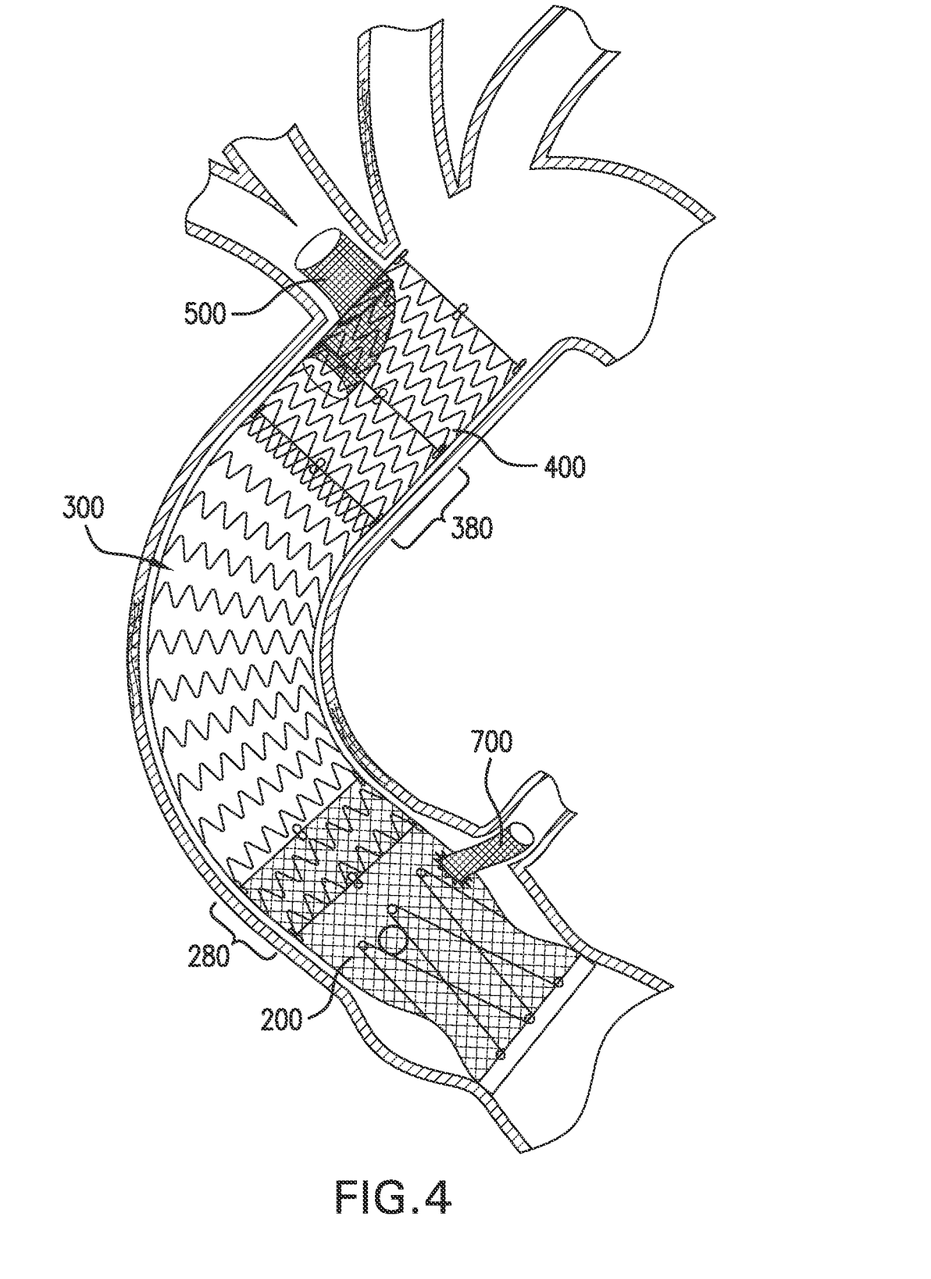

In some embodiments (as shown in FIGS. 3-4) the proximal end of the brachiocephalic graft 400 is inserted within the distal end of endovascular graft 300 such there is an overlap region 380 between the two components. In some embodiments, the overlapping region between the adjacent components is a distance of about 2 cm or greater. In this regard, the brachiocephalic graft. 400 can have a larger (expanded) diameter than the endovascular graft 300 to ensure an adequate (e.g. interference fit) seal.

Similarly to the radiopaque markers 1000 discussed above with respect to endovascular graft 300, each end of the brachiocephalic graft 400 component can incorporate four radio-opaque markers positioned 90 degrees apart. This allows for accurate placement with respect to the distal or proximal positioning of the stent graft, as well as for accurate circumferential positioning of the brachiocephalic graft 400 ends in the event the physician needs to rotate the brachiocephalic graft 400 with respect to one of the other components (e.g. stent graft 300, anchoring stent 500).

The brachiocephalic graft 400 includes a bifurcated "graft-in-graft" configuration, whereby the main lumen of brachiocephalic graft 400 has a side-branched tunnel 402 leading to an aperture perpendicular to the distal opening end 422. The side-branched tunnel 402 opens to an orifice with a radio-opaque circumference that faces the brachiocephalic artery (when deployed within a patient). This brachiocephalic graft 400 component is deployed proximally from the distal ascending aorta within the stent graft 300 to distally past the brachiocephalic artery orifice, but proximal to the left common carotid artery orifice.

Anchoring Stent

In accordance with another aspect of the disclosure, an optional additional expandable anchoring stent 500 can be employed and coupled to brachiocephalic graft 400. An exemplary embodiment of such an optional anchoring stent 500 is shown in FIGS. 3-4 which depicts the anchoring stent 500 partially disposed within the branched lumen 402 of brachiocephalic graft 400.

The anchoring stent 500 can be constructed in a similar manner as the grafts 300 and 400 as discussed above (though need not include the overlying or woven graft material). As discussed above, the various components proximal to the anchoring stent (i.e. brachiocephalic graft 400, endovascular graft 300 and valve member 200) are either integrally formed or coupled to each other (e.g. via the structural retention features).

As shown in FIGS. 3-4, anchoring stent 500 can be formed with a curve or bend of up to 90 degrees between its proximal and distal ends. This curve or bend allows the proximal end of anchoring stent 500 to extend into and align with the main lumen of the brachiocephalic graft 400, while the distal end of anchoring stent 500 extends towards and is aligned with the brachiocephalic artery. In the embodiment shown in FIGS. 3-4, the anchoring stent 500 is bent such that the exterior surface of anchoring stent 500 abuts the interior surface of endovascular graft 300. Accordingly the lumen of anchoring stent 500 is in fluid communication with the lumen of brachiocephalic graft 400. Similar to the other interference fit couplings described above, the expanded diameter of stent 500 can be larger than the opening of aperture 402 to create a secure union therebetween.

Likewise, the diameter of stent 500 can be larger than the diameter of the patient's anatomy such that the stent rings press against the walls, thereby serving as an anchor to secure the entire device (i.e. valve 200, graft 300, brachiocephalic graft 400) in place. Moreover, the larger cross-sectional area of the stent 500 reduces the chance of tissue by distributing the contact force between the multiple rings which make up the anchoring stent 500 and the tissue over a larger contact area. This larger area is advantageous as compared to prior art anchoring devices (e.g. hooks and barbs) as the increased surface area of stent 500 reduces the localized peak force on the tissue and reduces the likelihood that damage will occur.

When properly positioned, the anchoring stent 500 is then deployed proximally from within the side-branched tunnel 402 of brachiocephalic stent graft 400 distally to within the brachiocephalic artery, but proximal to the bifurcation into right subclavian and right common carotid artery. Accordingly, the brachiocephalic stent graft 400 allows complete sealing of the entry tear in type A aortic dissection. In this example, the brachiocephalic stent graft 400 is deployed in a distal-to-proximal fashion when accessed from the ventricular apex, and deployed in a proximal-to-distal fashion when accessed by other approaches. When approached from the ventricular apex, the anchoring stent 500 is deployed in a distal-proximal fashion from the brachiocephalic artery into the branched tunnel 402 within the brachiocephalic stent graft 400. When approached from the other access sites, the covered stent can be deployed in either distal-proximal or proximal-distal fashion. As discussed above, the brachiocephalic graft 400 and the anchoring stent 500 can also include structural retention features (e.g. magnetic couplers) to connect the two components together.

Valve Member

In accordance with another aspect of the disclosure, a valve member 200 is provided which includes a transcatheter heart valve.

The valve member 200 includes a valve 250, and an elongate tubular portion having a proximal end 224 and a distal end 222 defining a length therebetween, the elongate tubular portion having at least one aperture 202 disposed in a sidewall at a location between the proximal and distal ends, and a plurality of leaflets 252. In some embodiments the valve member is configured as a self-expanding component.

The elongate tubular portion of the valve member 200 can be constructed in a similar manner as the endovascular graft 300, as described above, with the aperture 202 being free of any graft material or structural members from the expandable frame so as to permit free unobstructed flow of blood through the aperture 202. The heart valve 200 may be fully covered with graft material except the apertures designed to access and perfuse the coronary arteries, or alternatively be partly covered with graft material to allow perfusion of the coronary arteries from the openings of frame lattice structure. In an exemplary embodiment, the valve includes three identical biodegradable or biological leaflets 252 mounted on a self-expandable frame. For example, the leaflets can be formed of pericardium or extracellular matrix. Additionally, radio-opaque markers can be located on the valve member at the nadir of each of the three valve leaflets and each of the three commissures to provide optimal alignment and orientation during device positioning. Additionally or alternatively, the apertures 202 can incorporate a circumferential radio-opaque rigid ring, to allow accurate landmark under fluoroscopy and provide adequate blood flow to the native left main coronary artery during device deployment.

In some embodiments, the proximal end of the valve member consists of a sealing member (e.g. proximally extending skirt) 244 made of synthetic material that is designed to minimize paravalvular leak. The skirt 244 is formed with sufficient flexibility that it can conform to the native aorta-ventricular junction that may or may not expand with blood flow or temperature differential.

Figure 7A:
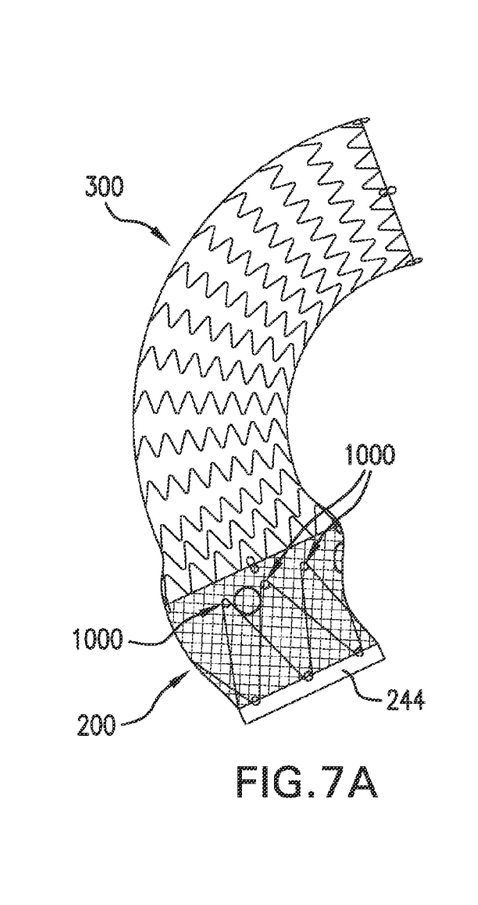
FIGS. 7A-C are schematic representations of various valve member and stent grafts of the medical device disclosed herein.
Figure 7B:
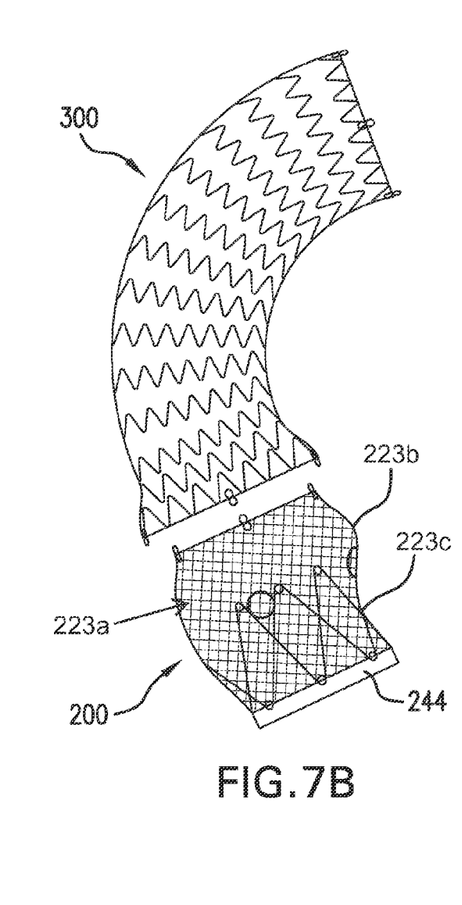
Figure 7C:
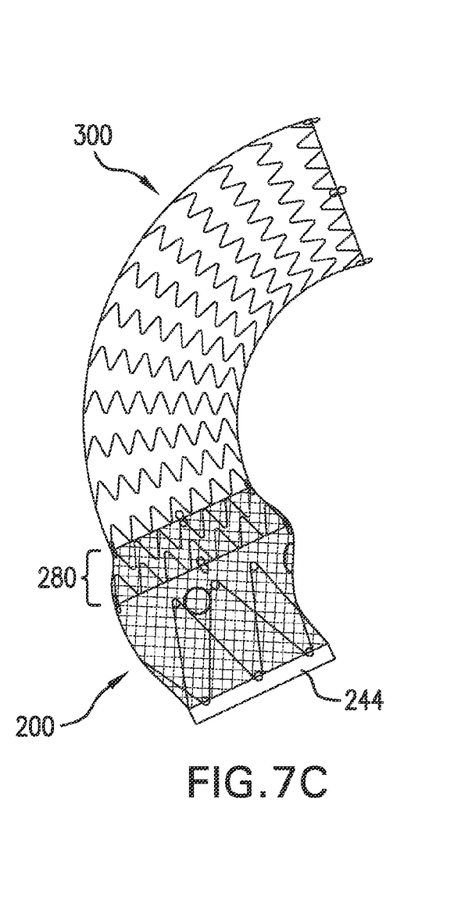

In some embodiments, as shown in FIGS. 4 and 7C, the proximal end of the endovascular graft 300 is inserted within the distal end of valve member 200 such there is an overlap region 280 between the two components. In some embodiments, the overlapping region between the adjacent components is a distance of about 5 mm or greater (depending on whether the proximal end of the endovascular graft is an exposed bare metal stent construction or includes a graft material, as discussed above). In this regard, the endovascular graft 300 can have a larger (expanded) diameter than the valve member 200 to ensure an adequate (e.g. interference fit) seal. As discussed above, the endovascular graft 300 and the valve member 200 can also include structural retention features (e.g. magnetic couplers) to connect the two components together.

The aperture(s) 202 can serve as coronary orifices in which they are located at the level of the valve commissures in order to provide ongoing blood flow to the native coronary arteries. In the embodiment shown in FIG. 3-6 the aperture(s) are located at a midpoint between the proximal and distal ends of valve member 200. In one embodiment, the apertures 202 are positioned in a downward (or proximal) facing manner (as shown in FIG. 7A). As described above with respect to the other components of the disclosure, circumferentially spaced radio-opaque materials can be incorporated at the proximal and distal ends of the valve member 200, coronary orifices 202 of the valve member 200, as well as the valve component 250 of the device, to enable accurate deployment of the coronary stent grafts (or "covered stents") 700 through the orifices 202 into the two coronary ostia. Similarly, a plurality (e.g. four) radio-opaque markers 1000 can be positioned at 90 degrees apart at a predetermined longitudinal distance from the leaflet commissures.

Valve Member Contour

The elongate tubular portion of the valve member 200 can be configured with a non-uniform (e.g. tapered contour) geometry. In some embodiments the proximal end 224 and distal end 222 of the elongate tubular portion of the valve member 200 have a first diameter, and a midpoint of the elongate tubular portion of the valve member has a smaller diameter. In the exemplary embodiment shown in FIGS. 3-6 the valve member 200 has a tapered or reduced diameter such that the valve member exhibits a concave contour at a point between the proximal and distal ends. In some embodiments the maximum point of taper (i.e. location with the smallest diameter) is proximate the aperture(s) 202 and leaflet commissures. As shown in FIGS. 3-6 this point of maximum taper is a predetermined distance below the proximate the aperture(s) 202 and leaflet commissures. The maximum taper is preferably wide enough to accommodate the valve leaflets to open fully at end-systole of the cardiac cycle. The apertures are preferably close or on the same level or height as the valve commissures to avoid coronary blood flow obstruction and allow wire access to the coronary arteries. The height of the aortic sinus (from annulus to sinotubular junction averages 18+/−3 mm and coronary artery height (bottom edge) averages 12-13+/−2.5 mm from the annulus. To ensure the aperture is distal to the coronary artery height, the spacing between the apertures and the point of maximum taper in an exemplary embodiment is 3-5 mm. In some embodiments, the point of maximum taper is located at midpoint between the aortic valve annulus and sinotubular junction. Such a configuration minimizes the risk of leaflets of the valve member in contact with the tubular wall during opening and also give the most space for the aperture be open to access to the coronary arteries.

In other embodiments, the contour can include at least a portion of the valve member having a concave shape. In some embodiments the valve member can be configured with a combination of convex and concave contours. For example and as shown in FIGS. 7A-C, the valve member 200 has a contour in which the non-coronary sinus portion of the frame exhibits a convex contour 223a and is apposed to the non-coronary sinus of the aortic wall, while part of the frame containing the aperture facing right- and left-coronary sinus is formed with a convex shape 223b to mimic distal sinus of Valsalva and a concave shape 223c to accommodate the native aortic valve leaflet in order to avoid coronary artery obstruction, while providing access to the coronary arteries.

As noted above, the expandable frame of the valve member can be fully covered by a graft material with apertures 202, or alternatively only partially covered by a graft material including the side facing the non-coronary sinus and lower portion of the frame facing the right- and left-coronary sinus, so as to optimize tissue apposition and prevent blood flow tracking between the frame and the aortic wall. In the case of a partially covered frame, the opening of each cell within the uncovered portion of the frame can be large enough for access to the coronary artery.

Additionally, the self-expanding valve can be deployed over the native aortic valve such that (via the expansion of the self-expanding valve member 200) the native leaflets are displaced without occluding the coronary artery orifices.

Figure 8A:
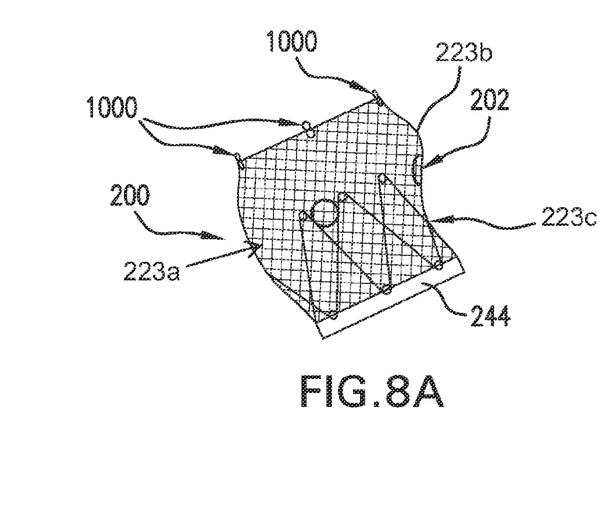
FIGS. 8A-B are schematic representations of various valve member of the medical device disclosed herein.
Figure 8B:
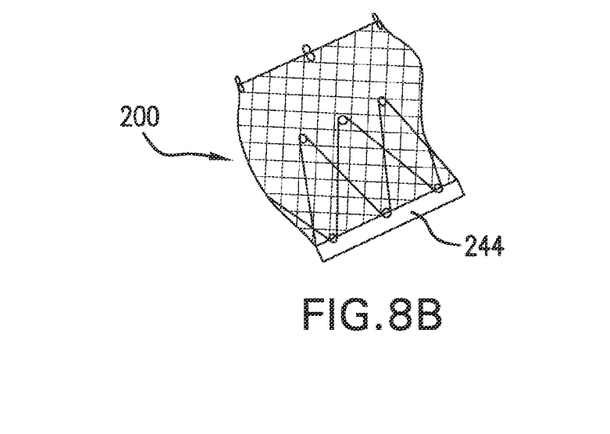
Figure 9A:
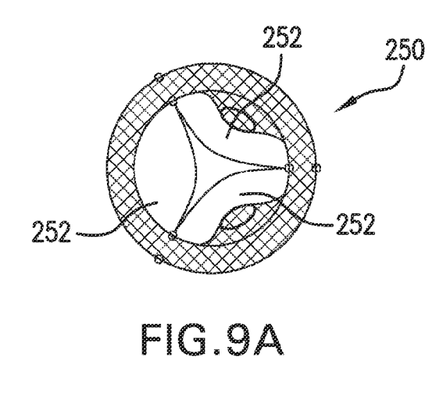
FIGS. 9A-B are schematic representations of various valve members of the medical device disclosed herein.
Figure 9B:
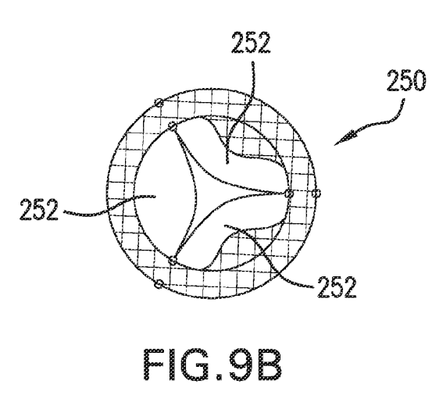

In some embodiments, as shown in FIGS. 7-9, the proximal end of the endovascular graft component 300 of the disclosed device is located (when deployed) proximal to the sinotubular junction and includes a portion having an increased diameter which serves as a "skirt" or sealing member. This allows better anchoring of the device against this anatomical location. Radio-opaque markers will be located at the junction to denote the tapering and the beginning of the ascending aorta portion of the stent graft 300, thereby allowing accurate device deployment.

Coronary Stent Grafts or "Covered Stents"

Coronary stent grafts 700 can be constructed in a similar manner to the endovascular graft 300, described above. Additionally, coronary stent grafts 700 can be formed with a flared end to facilitate coupling with the orifices 202 in valve member 200. In such embodiments, the flared end 722 has a diameter which is equal to or larger than the orifice 202 such that the coronary stent graft 700 remains external or co-planar (e.g. flush) with the valve member 200 and does not protrude into the inner lumen of valve member 200.

Delivery System

In accordance with another aspect of the disclosure the delivery system includes, for an integrally formed unitary device, an introducer sheath and a delivery sheath which contains the crimped device. The delivery sheath can also contain the stents 700 for bridging the two coronary arteries. For embodiments in which the device is formed as separate discrete components (i.e. endovascular stent graft, transcatheter heart valve) which require assembly, the delivery device includes an introducer sheath, and a delivery sheath consisting of the stent graft, a delivery sheath consisting of the transcatheter heart valve, and delivery sheaths consisting of the covered stents for bridging the two coronary arteries. Each of these delivery sheaths can be configured with separate and discrete lumens. Each of the components in the above delivery system configurations will have a specific design for access from the ventricular apex, thoracic aorta, and peripheral and neck arteries aforementioned. Additionally, the introducer and delivery sheaths of the delivery system can be made of plastic or similar composite materials that are disposable after the procedure.

Method of Delivery

Figure 5:
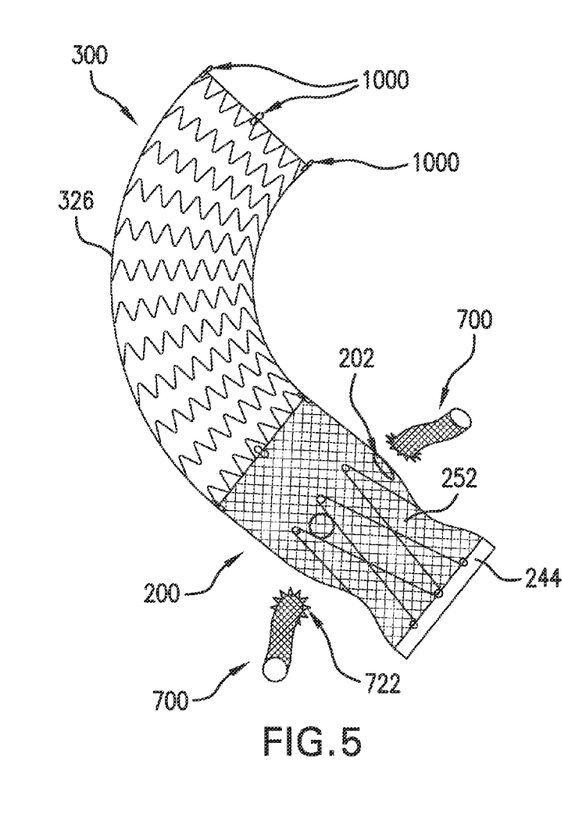
FIGS. 5-6 are schematic representations of exploded views of the medical device disclosed herein.

In accordance with another aspect of the disclosure, the device can be delivered and deployed from several approaches including but not limited to the left ventricular apex (FIG. 5, circle A), femoral and iliac arteries (FIG. 5, circles H, I), axillary and subclavian arteries (FIG. 6, circles C, G), carotid (FIG. 5, circles E, F) and brachiocephalic (FIG. 5, circle D) arteries, and thoracic aorta (FIG. 5, circle B). Access to the above structures can be secured by deploying a surgical or percutaneous access and closure device specific to the access site of choice.

Left Ventricular Apex

In one approach, the device disclosed herein can be delivered and deployed via the left ventricular apex. In such approaches, the left ventricular apex is visualized and accessed, for example, via a left anterior mini-thoracotomy or thoracoscopy with an endoscope. The apex is identified under direct visualization and fluoroscopy and the entry point is secured via a percutaneous access and closure device or by surgical placement of sutures. An introducer sheath is then placed through the apex in an antegrade fashion after a guidewire has already been passed across the aortic valve into the descending thoracic aorta.

The delivery sheath containing the device is inserted through the introducer sheath in an antegrade fashion and the proximal end of the device is positioned at the junction of the left ventricular outflow tract and aortic valve annulus under live fluoroscopy. Using live fluoroscopy, real-time overlay software and transesophageal echocardiography guidance facilitates positioning the device according to the anatomic and device landmarks, the device is deployed in a proximal-to-distal direction from the aortic valve annulus towards the distal ascending aorta, under rapid ventricular pacing and apnea. After confirmation of optimal positioning of the device, coronary stent grafts 700 are deployed in a similar fashion into the coronary artery ostia to cover the coronary orifices of the composite device in order to bridge the coronary artery blood flow and seal off blood flow into the native aortic root.

A method for delivering and deploying the device, when constructed as a plurality of discrete components for assembly, can be performed in a plurality (e.g. 2) of stages. First, the delivery sheath containing the valve member 200 is inserted through the introducer sheath in an antegrade fashion and the proximal end is positioned at the junction of the left ventricular outflow tract and aortic valve annulus under live fluoroscopy. Using live fluoroscopy, real-time overlay software and transesophageal echocardiography guidance facilitates positioning the valve device according to the anatomic and device landmarks, the valve device is then deployed in a proximal-to-distal direction from the aortic valve annulus towards the proximal ascending aorta, under rapid ventricular pacing and apnea.

After confirmation of optimal positioning of the device, the valve delivery sheath is removed and the second stage involves inserting the delivery sheath containing the endovascular graft 300 in an antegrade fashion with the proximal end positioned with a defined length of overlap of the valve member 200 at the proximal ascending aorta. Using live fluoroscopy, real-time overlay software and transesophageal echocardiography guidance facilitates positioning the device according to the anatomic and device landmarks, the stent graft component is then deployed in a proximal-to-distal direction from the proximal towards the distal ascending aorta, under rapid ventricular pacing and apnea. After confirmation of optimal positioning of the device, coronary stent grafts 700 are deployed in a similar fashion into the coronary artery ostia to cover the coronary orifices of the composite device to bridge the coronary artery blood flow and seal off blood flow into the native aortic root.

Femoral or Iliac Artery

In another approach the device can be delivered and deployed via the femoral or iliac artery, axillary or subclavian artery, carotid or brachiocephalic artery. In such approaches an introducer sheath is placed through the selected artery in a retrograde fashion after a guidewire has already been passed across the aortic valve into the left ventricular cavity.

For an integrally formed unitary device, the delivery sheath containing the device is inserted through the introducer sheath in a retrograde fashion and the proximal end of the device is positioned at the junction of the left ventricular outflow tract and aortic valve annulus under live fluoroscopy. The rest of the procedure is performed in a similar manner as described above, with the remaining components delivered to the aortic root in a retrograde fashion.

For a multi-component device, the implantation of the invention is performed in a plurality (e.g. 2) stages. First, the delivery sheath containing the valve member 200 is inserted through the introducer sheath in a retrograde fashion and the proximal end is positioned at the junction of the left ventricular outflow tract and aortic valve annulus under live fluoroscopy. Using live fluoroscopy, real-time overlay software and transesophageal echocardiography guidance to facilitate positioning the valve device according to the anatomic and device landmarks, the valve device is deployed in a proximal-to-distal direction from the aortic valve annulus towards the proximal ascending aorta, under rapid ventricular pacing and apnea. After confirmation of optimal positioning of the device, the valve delivery sheath is removed and the second stage involves inserting the delivery sheath containing the endovascular graft 300 in a retrograde fashion with the proximal end positioned with a defined length of overlap of the valve member 200 at the proximal ascending aorta. The rest of the procedure is performed in a similar manner as described above, with the remaining components delivered to the aortic root in a retrograde fashion.

Thoracic Aorta

In another approach the device can be delivered and deployed via thoracic aorta with visualization and access via a hemisternotomy, full median sternotomy or right anterior minithoracotomy. The entry point of the aorta is secured via a percutaneous access and closure device or via surgical placement of sutures. An introducer sheath designed for aortic access is placed through the thoracic aorta in a retrograde fashion after a guidewire has already been passed across the aortic valve into the left ventricular cavity. The rest of the procedure is performed in a similar fashion as described in the femoral or iliac artery approach above, except the delivery sheaths containing the devices and device components will be specific to access via the thoracic aorta.

Aortic Arch

In accordance with another aspect of the disclosure, the device can be configured as an endovascular prosthesis designed to repair or replace the aortic arch so as to effectively seal off and to treat an aneurysm or dissection. In one embodiment the device is configured to be deployed across the aortic arch, with proximal anchorage in the ascending aorta or an aortic graft (with or without stent), and distal anchorage in the proximal descending thoracic aorta or an aortic graft (with or without stent). As discussed above, the aortic arch device can be constructed either as an integral unit or as separate and discrete components for assembly.

The aortic arch device 600 includes a generally cylindrical and expandable frame which can be constructed in a similar manner as endovascular graft 300 discussed above, with a proximal end configured for deployment within the ascending aorta, the distal end configured for deployment in the descending thoracic aorta. The graft material of the aortic arch component 600 extends over a portion of the expandable frame to define an opening disposed between the proximal end and distal end. The opening 602 allows blood flow transverse to the longitudinal lumen of the graft member 600. In some embodiments the boundary edge of this opening includes radiopaque markers circumscribing the opening. Although the embodiment illustrated depicts an elliptical opening 602, the size and shape of the opening can vary. For example, a plurality of discrete openings can be formed, with each opening corresponding to one of the arteris. This exemplary aortic arch component 600 can be deployed with the various components discussed above (e.g., valve member 200, endovascular graft 300) with the aggregate device being formed as an integral unit, or plurality of discrete components for assembly.

Figure 10:
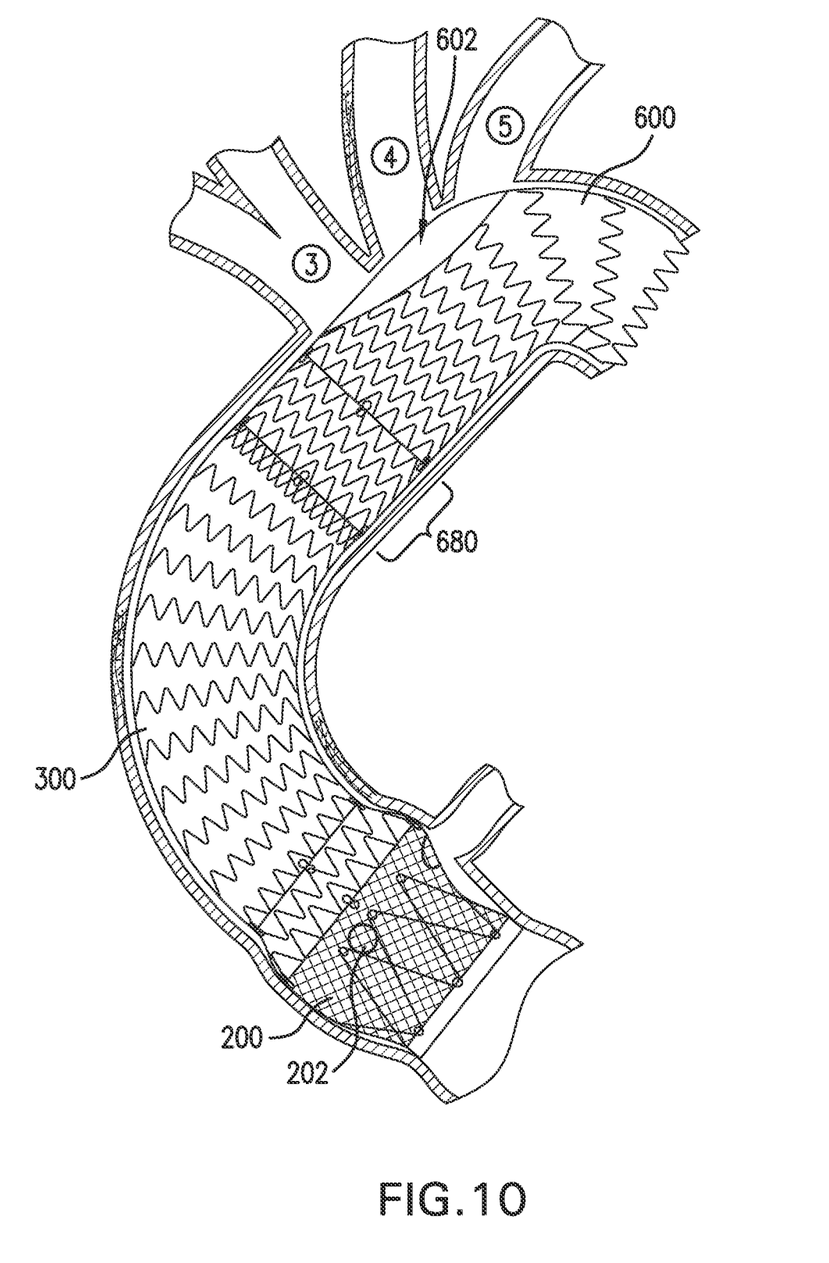
FIG. 10 is a schematic representation of the medical device of FIG. 5 in combination with an aortic arch graft as disclosed herein.
Figure 11:
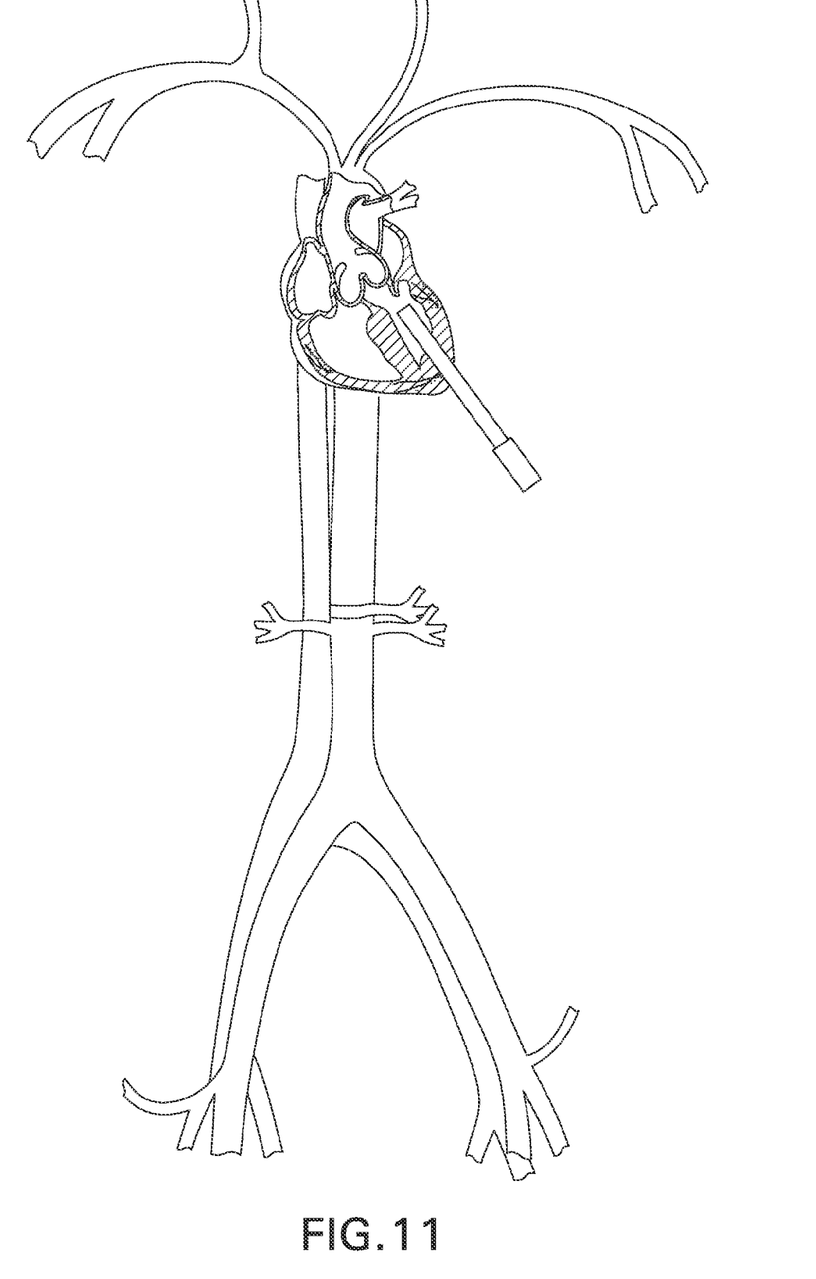
FIG. 11 is schematic representations of an exemplary delivery method for the medical device disclosed herein.

These radiopaque markers allow precise placement of the aortic arch component 600, and in particular allows the opening 602 within the graft material to be precisely placed in a corresponding position, or adjacent, to the brachiocephalic artery (3), the left common carotid artery (4), and the left subclavian artery (5) as shown in FIG. 10. The opening 602 is sized to extend across each of these arteries such that there is no graft material present to inhibit or occlude blood flow between these arteries and the inner lumen of the device 600. Instead only the bare metal struts of the expandable frame are present across these arteries. Additionally, in some embodiments the underlying (or interwoven) expandable frame of the aortic arch component 600 can be formed with an "open cell" design in which the struts or annular rings which form the lattice of the aortic arch component are absent across this opening 602. The absence of any struts and graft material reduce the likelihood of obstruction or interference with blood flow through the aortic graft component 600.

The aortic arch graft 600 can also include anchor members (e.g. self-expanding stents or grafts) partially extending into the proximal and distal ends thereof. As discussed above, the aortic arch graft 600 can also include interference fit connections and/or structural retention features which connect the adjacent components together. For example, the aortic arch graft 600 for deployment in the thoracic aorta can be coupled with the proximal anchorage into another expandable stent/graft, whereby the proximal end of the anchoring stent/graft is located at or just distal to the origin of the left subclavian artery (5). In some embodiments, the overlapping region 680 between the adjacent components is a distance of about 2.0 cm or greater.

The proximal and distal ends of the aortic arch graft 600 (and any anchoring members present) can also include radiopaque markers as described above to facilitate positioning (i.e. longitudinal as well as circumferential) of the components.

While the disclosed subject matter is described herein in terms of certain preferred embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A medical device comprising:
    a valve member, the valve member including:
        an elongate tubular portion having a proximal end and a distal end defining a length therebetween, the elongate tubular portion having at least one aperture disposed in a sidewall at a location between the proximal and distal ends, and
        a plurality of leaflets,
    a first endovascular graft having a proximal end and a distal end defining a length therebetween and an opening at the proximal and distal ends, the first endovascular graft configured for coupling to the valve member;
    a second endovascular graft having a proximal end and a distal end defining a length therebetween and an opening at the proximal and distal ends, the second endovascular graft having a bifurcated lumen including a main lumen extending the length of the graft and a branched lumen longitudinally offset to a side of the main lumen, the second endovascular graft configured for coupling to the first endovascular graft; and
    an expandable anchor member having a proximal end and a distal end defining a length therebetween and an opening at the proximal and distal ends, the expandable anchor member configured for coupling to the second endovascular graft with the proximal end of the expandable anchor member disposed within the main lumen and between the proximal and distal ends of the second endovascular graft, and the distal end of the expandable anchor member extending outward from the second endovascular graft at a location between the proximal and distal ends of the second endovascular graft.

2. The medical device of claim 1, wherein the elongate tubular portion of the valve member has a non-uniform geometry.

3. The medical device of claim 1, wherein the proximal end and distal end of the elongate tubular portion of the valve member have a first diameter, and a midpoint of the elongate tubular portion of the valve member has a second diameter.

4. The medical device of claim 1, wherein the elongate tubular portion of the valve member has a tapered contour.

5. The medical device of claim 1, wherein the at least one aperture in the elongate tubular portion of the valve member is disposed proximate a midpoint between the proximal and distal ends of the elongate tubular portion.

6. The medical device of claim 1, wherein the valve member and first endovascular graft are formed as an integral unit.

7. The medical device of claim 1, wherein the valve member, first endovascular graft, second endovascular graft, and expandable anchor member are formed as separate components.

8. The medical device of claim 1, wherein the valve member is self-expanding.

9. The medical device of claim 1, wherein the expandable anchor member is a self-expanding stent, with a distal end offset by an angle of approximately 90 degrees with respect to the proximal end.

10. The medical device of claim 1, wherein the second endovascular graft includes a sidewall aperture at a location disposed between the proximal and distal ends thereof.

11. The medical device of claim 10, wherein the expandable anchor member is in fluid communication with the sidewall aperture of the second endovascular graft.

12. The medical device of claim 1, further comprising a seal member disposed at a proximal end of the valve member.

13. A medical device comprising:
   a valve member, the valve member including:
      a plurality of leaflets, adjacent leaflets joined at valve commissures, and an elongate tubular portion having a proximal end and a distal end defining a length therebetween and a graft material extending over at least a portion of the tubular portion, the elongate tubular portion having at least one aperture disposed in a sidewall at a location proximate the valve commissures,
   a first endovascular graft having a proximal end and a distal end defining a length therebetween and an opening at the proximal and distal ends, the proximal end of the first endovascular graft configured for coupling to the valve member;
   at least one coronary stent, the at least one coronary stent configured for coupling to the at least one aperture of the elongate tubular portion of the valve member;
   wherein the proximal end and distal end of the elongate tubular portion of the valve member have a first diameter, and a midpoint of the elongate tubular portion of the valve member has a second diameter, with a smallest diameter located proximate the at least one aperture.

14. The medical device of claim 13, wherein the valve member and first endovascular graft are formed as an integral unit.

15. The medical device of claim 13, wherein the at least one coronary stent has a first end with a diameter equal to or larger than a diameter of the at least one aperture of the valve member.

16. The medical device of claim 15, wherein the at least one coronary stent includes a flared end, the flared end coupled to the elongate tubular portion of the valve member.

* * * * *